US006813337B2

(12) United States Patent
Svatos et al.

(10) Patent No.: US 6,813,337 B2
(45) Date of Patent: Nov. 2, 2004

(54) REMOVABLE ELECTRON MULTILEAF COLLIMATOR

(75) Inventors: Michelle Marie Svatos, Oakland, CA (US); William F. Collins, Clayton, CA (US)

(73) Assignee: Siemens Medical Solutions USA, Inc, Melvern, PA (US)

( * ) Notice: Subject to any disclaimer, the term of this patent is extended or adjusted under 35 U.S.C. 154(b) by 36 days.

(21) Appl. No.: 09/909,513

(22) Filed: Jul. 20, 2001

(65) Prior Publication Data

US 2003/0202632 A1 Oct. 30, 2003

(51) Int. Cl.[7] .............................................. G21K 1/04
(52) U.S. Cl. ........................................ 378/65; 378/151
(58) Field of Search .................................. 378/65, 151

(56) References Cited

U.S. PATENT DOCUMENTS

| | | | | |
|---|---|---|---|---|
| 4,220,866 A | * | 9/1980 | Taumann et al. | 250/511 |
| 5,160,847 A | * | 11/1992 | Leavitt et al. | 378/65 |
| 6,167,114 A | * | 12/2000 | Siochi | 378/65 |

FOREIGN PATENT DOCUMENTS

| | | |
|---|---|---|
| JP | 7116276 A | 5/1995 |
| JP | 11216196 A | 8/1999 |
| JP | 2001276238 A | 10/2001 |
| WO | WO 00/13189 | 3/2000 |

OTHER PUBLICATIONS

Ma et al., "Energy and intensity–modulated electron beams for radiotherapy" (IOP Publishing Ltd, vol. 45, No. 8, Aug. 1, 2000; pp. 2293–2311).

Karisson et al. "Treatment head design for multileaf collimated high–13 energy electrons" (Medical Physics, vol. 26, No. 10, Oct. 1999, pp. 2161–2167).

Moran et al. "Characteristics of scattered electron beams shaped with a multileaf collimator" (Medical Physics, vol. 24, No. 9, Sep. 1997; pp. 1491–1498).

Zhu et al. "Characteristics of bremsstrahlung in electron beams" (Medical Physics, vol. 28, No. 7, Jul. 2001; pp. 1352–1358).

\* cited by examiner

*Primary Examiner*—Craig E. Church

(57) ABSTRACT

A removable electron collimator for use in collimating an electron beam in a radiation therapy device is provided, where the collimator includes drive electronics, removably mounted on an exterior of an accessory tray of the radiation therapy device. The electron collimator also includes a plurality of leaves positionable by the drive electronics to move across a path of the electron beam, the plurality of leaves removably mounted on the accessory tray of the radiation therapy device.

19 Claims, 4 Drawing Sheets

REMOVABLE ELECTRON MULTILEAF COLLIMATOR

CROSS-REFERENCE TO RELATED APPLICATIONS

This application is related to commonly owned U.S. patent application Ser. No. 09/909,589, filed Jul. 20, 2001 (on even date herewith), for "AUTOMATED DELIVERY OF TREATMENT FIELDS", and U.S. patent application Ser. No. 09/910,526, filed Jul. 20, 2001 (on even date herewith), for "VERIFICATION OF ELECTRON TREATMENT FIELDS", the contents of each of which are incorporated by reference in their entirety for all purposes.

BACKGROUND OF THE INVENTION

1. Field of the Invention

The present invention relates generally to radiation therapy devices, and more particularly, to a removable electron multileaf collimator for use in a radiation therapy device.

2. Description of the Related Art

Conventional radiation therapy typically involves directing a radiation beam at a tumor in a patient to deliver a predetermined dose of therapeutic radiation to the tumor according to an established treatment plan. This is typically accomplished using a radiation therapy device such as the device described in U.S. Pat. No. 5,668,847 issued Sep. 16, 1997 to Hernandez, the contents of which are incorporated herein for all purposes.

The radiotherapy treatment of tumors involves three-dimensional treatment volumes which typically include segments of normal, healthy tissue and organs. Healthy tissue and organs are often in the treatment path of the radiation beam. This complicates treatment, because the healthy tissue and organs must be taken into account when delivering a dose of radiation to the tumor. While there is a need to minimize damage to healthy tissue and organs, there is an equally important need to ensure that the tumor receives an adequately high dose of radiation. Cure rates for many tumors are a sensitive function of the dose they receive. Therefore, it is important to closely match the radiation beam's shape and effects with the shape and volume of the tumor being treated.

Both primary photon and primary electron beams may be used in radiation therapy. Accordingly, many existing radiation therapy devices include the ability to generate and deliver both photon and electron beams. Currently, clinical practice requires substantial manual intervention to use conformal electron treatment. Conformal photon fields typically are shaped using one or more collimating devices positioned between the source and the treatment area. Many of these photon beam collimating devices may be positioned automatically to deliver a desired photon field shape to a treatment area on a patient. Little manual intervention is required to administer photon radiation therapy.

Primary electrons are currently used on approximately 30% of all patients who undergo radiation therapy. Electron fields delivered via radiation therapy devices are typically shaped using either an off-the-shelf electron applicator (either rectangular or circular in cross-section) or a custom cutout formed of Cerrobend®. Both of these beam shaping methods have limitations. Off-the-shelf electron applicators often unnecessarily irradiate portions of healthy tissue, since they do not precisely conform to the target. Custom cutouts formed of Cerrobende are highly conformal, but are costly to make, store and require special quality assurance. The Cerrobend® material may also require special handling because of the potentially toxic metals involved. Each of these approaches to electron field shaping also suffer in that they can be inefficient to use. A radiation therapist delivering a prescribed treatment must repeatedly enter the treatment room during treatment to insert the proper cutout for each field in the therapy. This is not only inefficient, but it effectively precludes the delivery of treatments which require electron field modulation in both intensity and energy at a single gantry position.

Oncologists would like to have the ability to prescribe mixed beam treatments which include the application of modulated electron and photon fields. With the exception of a few highly specialized and expensive devices, existing radiation therapy devices are unable to effectively provide such mixed beam treatments. Although existing radiation therapy devices do have the ability to deliver both electron and photon beams, the devices are unable to provide mixed beam treatments without requiring the repeated replacement and manual intervention by a therapist during treatment. It would be desirable to provide a radiation therapy device which is able to support mixed beam treatments where both photon and electron beams may be used in a single course of treatment and where the electron beam may be modulated in both intensity and energy without intervention by a radiation therapist. It would also be desirable to provide a system and method that allows the electron collimator assembly to be readily installed and removed as desired.

SUMMARY OF THE INVENTION

To alleviate the problems inherent in the prior art, and to allow the efficient and effective delivery of photon, electron, and mixed beam radiation therapy, embodiments of the present invention provide a system and method for use of a removable electron collimator.

According to one embodiment of the present invention, a radiation therapy device is provided which includes a radiation source positioned to direct a beam along a beam path toward a treatment area. The system includes a treatment head containing a first collimator controllable to selectively collimate the beam, and a second collimator removably positioned between the first collimator and the treatment area and controllable to selectively collimate the beam. In one embodiment, the second collimator is removably mounted on an accessory tray of the radiation therapy device. According to one embodiment, the first collimator is used to collimate a photon beam generated by the source, while the second collimator is used to collimate an electron beam generated by the source.

According to one embodiment of the present invention, an electron collimator for use in collimating an electron beam in a radiation therapy device is provided, where the collimator includes drive electronics, removably mounted on an exterior of an accessory tray of the radiation therapy device. The electron collimator also includes a plurality of leaves positionable by the drive electronics to move across a path of the electron beam, the plurality of leaves removably mounted on the accessory tray of the radiation therapy device.

The present invention is not limited to the disclosed preferred embodiments, however, as those skilled in the art can readily adapt the teachings of the present invention to create other embodiments and applications.

BRIEF DESCRIPTION OF THE DRAWINGS

The exact nature of this invention, as well as its objects and advantages, will become readily apparent from consideration of the following specification as illustrated in the accompanying drawings, in which like reference numerals designate like parts throughout the figures thereof, and wherein.

DETAILED DESCRIPTION

The following description is provided to enable any person skilled in the art to make and use the invention and sets forth the best modes contemplated by the inventor for carrying out the invention. Various modifications, however, will remain readily apparent to those skilled in the art.

Figure 1:
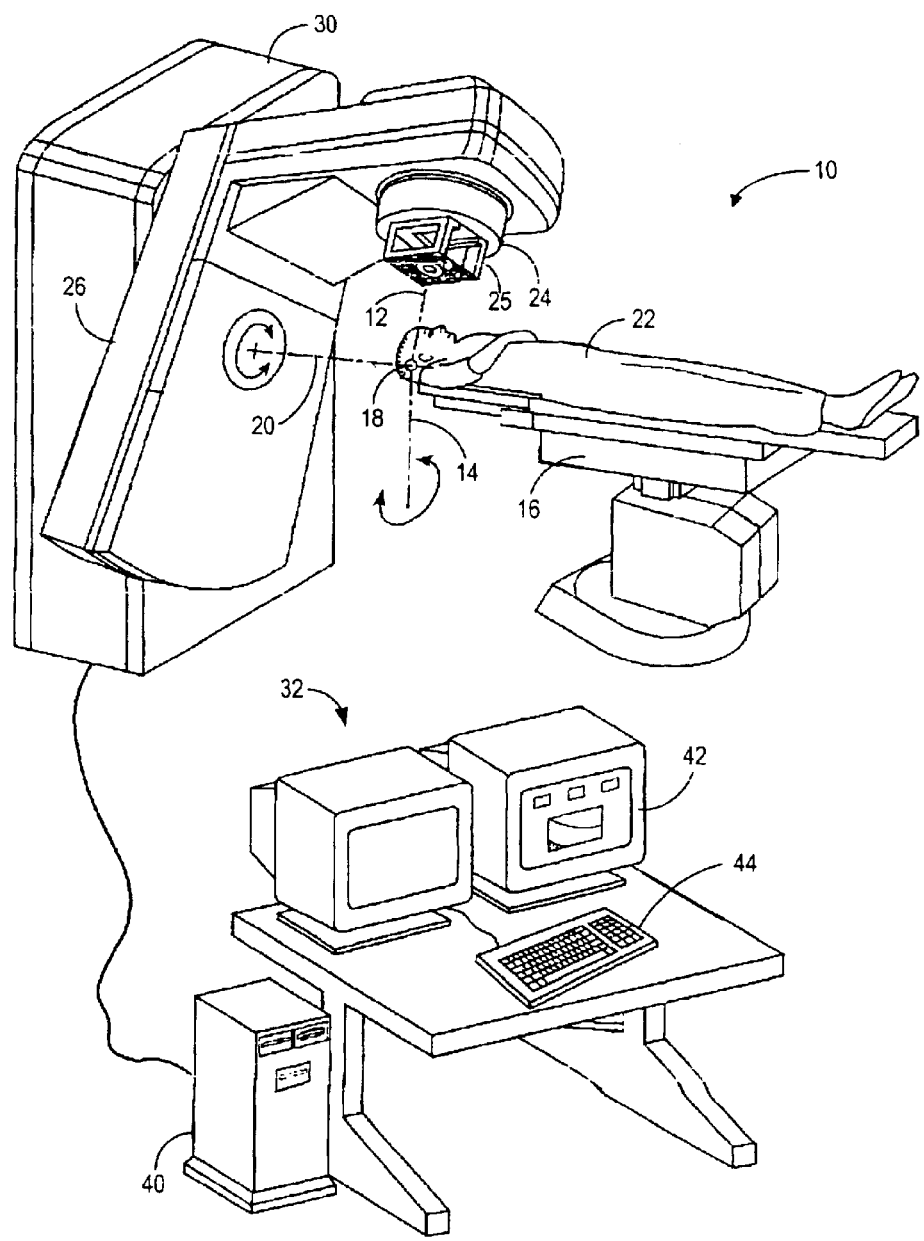
FIG. 1 is diagram illustrating a radiation therapy device.

Turning now to the drawings and, with particular attention to FIG. 1, a radiation therapy device 10 pursuant to embodiments of the present invention is shown. According to one embodiment of the present invention, radiation therapy device 10 includes a beam shielding device (not shown) within a treatment head 24, a control unit in a housing 30 and a treatment unit 32. An accessory tray 25 is mounted to an exterior of treatment head 24. Accessory tray 25, in one embodiment, is configured to receive and securely hold attachments used during the course of treatment planning and treatment (such as, for example, reticles, wedges, or the like).

Radiation therapy device 10 includes a gantry 26 which can be swiveled around a horizontal axis of rotation 20 in the course of a therapeutic treatment. Treatment head 24 is fastened to a projection of the gantry 26. A linear accelerator (not shown) is located inside gantry 26 to generate the high energy radiation required for the therapy. The axis of the radiation bundle emitted from the linear accelerator and the gantry 26 is designated by beam path 12. Electron, photon or any other detectable radiation can be used for the therapy. Embodiments of the present invention permit the controlled delivery of both primary electron and primary photon beams to a treatment zone 18 during the course of a prescribed treatment.

During a course of treatment, the radiation beam is trained on treatment zone 18 of an object 22, for example, a patient who is to be treated and whose tumor lies at the isocenter of the gantry rotation. The plates or leaves of the beam shielding device within the treatment head 24 are substantially impervious to the emitted radiation. The collimator leaves or plates are mounted between the radiation source and the patient in order to delimit (conform) the field. Areas of the body, for example, healthy tissue, are therefore subject to as little radiation as possible and preferably to none at all. The plates or leaves are movable such that the distribution of radiation over the field need not be uniform (one region can be given a higher dose than another). Furthermore, the gantry can be rotated so as to allow different beam angles and radiation distributions without having to move the patient.

According to one embodiment of the present invention, several beam shaping devices are used to shape radiation beams directed toward treatment zone 18. In one embodiment, a photon collimator and an electron collimator are provided. Each of these collimators, as will be described further below, may be separately controlled and positioned to shape beams directed at treatment zone 18. According to one embodiment, the photon collimator (not shown in FIG. 1) is contained within treatment head 24 and the electron collimator (not shown in FIG. 1) is removably mounted on accessory tray 25.

Radiation therapy device 10 also includes a central treatment processing or control unit 32 which is typically located apart from radiation therapy device 10. Radiation therapy device 10 is normally located in a different room to protect the therapist from radiation. Treatment unit 32 includes a processor 40 in communication with an operator console 42 (including one or more visual display units or monitors) and an input device such as a keyboard 44. Data can be input also through data carriers such as data storage devices or a verification and recording or automatic setup system. More than one control unit 32, processor 40, and/or operator console 42 may be provided to control radiation therapy device 10.

Treatment processing unit 32 is typically operated by a therapist who administers actual delivery of radiation treatment as prescribed by an oncologist. Therapist operates treatment processing unit 32 by using keyboard 44 or other input device. The therapist enters data defining the radiation dose to be delivered to the patient, for example, according to the prescription of the oncologist. The program can also be input via another input device, such as a data storage device. Various data can be displayed before and during the treatment on the screen of operator console 42.

Embodiments of the present invention permit the delivery of both primary electron and primary photon beams to treatment zone 18 during the course of a prescribed treatment. Embodiments of the present invention permit the creation and control of both photon and electron radiation beams which closely match the shape and size of treatment zone 18.

Figure 2:
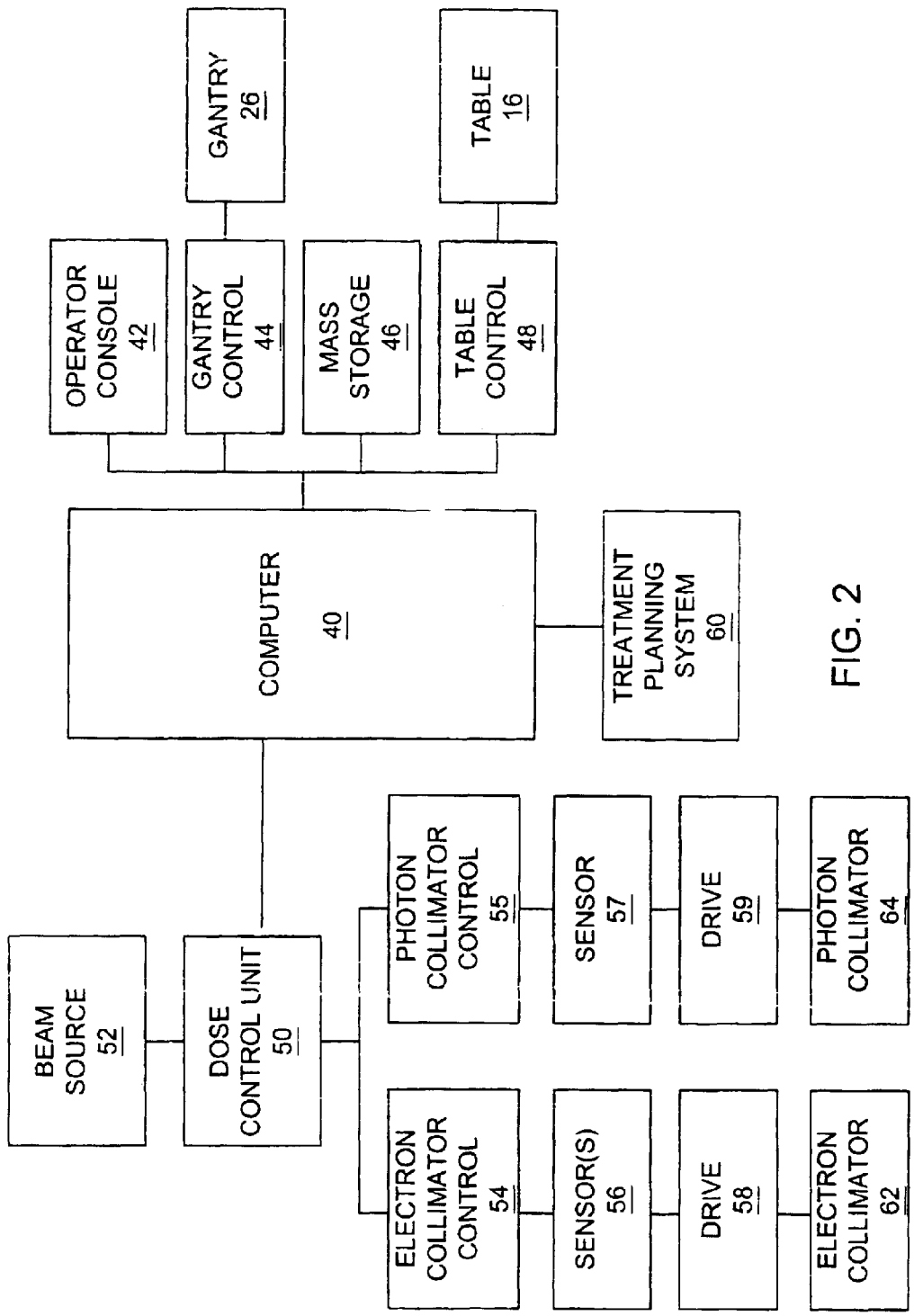
FIG. 2 is a block diagram illustrating portions of the radiation therapy device of FIG. 1 according to one embodiment of the present invention.

Referring now to FIG. 2, a block diagram is shown depicting portions of a radiation therapy device 10 and treatment unit 32 according to one embodiment of the present invention. In particular, treatment delivery elements of a radiation therapy device are shown, which may be configured in radiation therapy device 10 and treatment unit 32 as depicted in FIG. 1. The treatment delivery elements include a computer 40, operatively coupled to an operator console 42 for receiving operator control inputs and for displaying treatment data to an operator. Operator console 42 is typically operated by a radiation therapist who administers the delivery of a radiation treatment as prescribed by an oncologist. Using operator console 42, the radiation therapist enters data that defines the radiation to be delivered to a patient.

Mass storage device 46 stores data used and generated during the operation of the radiation therapy device including, for example, treatment data as defined by an oncologist for a particular patient. This treatment data is generated, for example, using a treatment planning system 60 which may include manual and computerized inputs to determine a beam shape prior to treatment of a patient. Treatment planning system 60 is typically used to define and simulate a beam shape required to deliver an appropriate therapeutic dose of radiation to treatment zone 18.

Data defining the beam shape and treatment are stored, e.g., in mass storage device 46 for use by computer 40 in delivering treatment. According to one embodiment of the present invention, treatment planning may include activities which occur prior to the delivery of the treatment, such as the generation of treatment data defining a photon treatment, an electron treatment, and/or a mixed beam treatment. Embodiments of the present invention permit the use of mixed beam treatments without the need for extended disruptions to install electron applicators or other shielding devices. Further, embodiments of the present invention permit field shaping of electron beams during a treatment in a device which also permits field shaping of photon beams during a treatment.

Although a single computer 40 is depicted in FIG. 2, those skilled in the art will appreciate that the functions described herein may be accomplished using one or more computing devices operating together or independently. Those skilled in the art will also appreciate that any suitable general purpose or specially programmed computer may be used to achieve the functionality described herein.

Computer 40 is also operatively coupled to various control units including, for example, a gantry control 44 and a table control 48. In operation, computer 40 directs the movement of gantry 26 via gantry control 44 and the movement of table 16 via table control 48. These devices are controlled by computer 40 to place a patient in a proper position to receive treatment from the radiation therapy device. In some embodiments, gantry 26 and/or table 16 may be repositioned during treatment to deliver a prescribed dose of radiation.

Computer 40 is also operatively coupled to a dose control unit 50 which includes a dosimetry controller and which is designed to control a beam source 52 to generate a desired beam achieving desired isodose curves. Beam source 52 may be one or more of, for example, an electron and/or photon beam source. Beam source 52 may be used to generate radiation beams in any of a number of ways well-known to those skilled in the art. For example, beam source 52 may include a dose control unit 50 used to control a trigger system generating injector trigger signals fed to an electron gun in a linear accelerator (not shown) to produce en electron beam as output. Beam source 52 is typically used to generate a beam of therapeutic radiation directed along an axis (as shown in FIG. 1 as item 12) toward treatment zone 18 on patient 22.

According to one embodiment of the invention, the beam generated by beam source 52 is shaped using one or more collimator assemblies, depending on the type of beam generated. For example, in one embodiment, a photon beam produced by beam source 52 is shaped by manipulating a photon collimator 64, while an electron beam produced by beam source 52 is shaped by manipulating an electron collimator 62. According to one embodiment, photon collimator 64 and electron collimator 62 are multi-leaf collimators having a plurality of individually-movable radiation blocking leaves. The leaves of each such collimator are individually driven by a drive unit 58, 59 and are positioned under the control of electron collimator control 54, photon collimator control 55 and sensor(s) 56 and 57.

Drive units 58, 59 move the leaves of each collimator in and out of the treatment field to create a desired field shape for each type of beam. In one embodiment, where an electron beam is to be generated and primary electrons are to be used in a treatment, photon collimator control 55 operates to retract individual leaves of photon collimator 64, while electron collimator control 54 operates to position individual leaves of electron collimator 62 across the path of the electron beam to generate a desired electron field shape at the isocenter. Similarly, in one embodiment, where a photon beam is to be generated and primary photons are to be used in a treatment, electron collimator control 54 operates to retract individual leaves of electron collimator 62 while photon collimator control 55 operates to position individual leaves of photon collimator 64 across the path of the photon beam to generate a desired photon beam field shape at the isocenter. In other embodiments, both collimators 62, 64 may be controlled in concert during the course of a treatment to generate a desired field shape at the isocenter.

Figure 3:
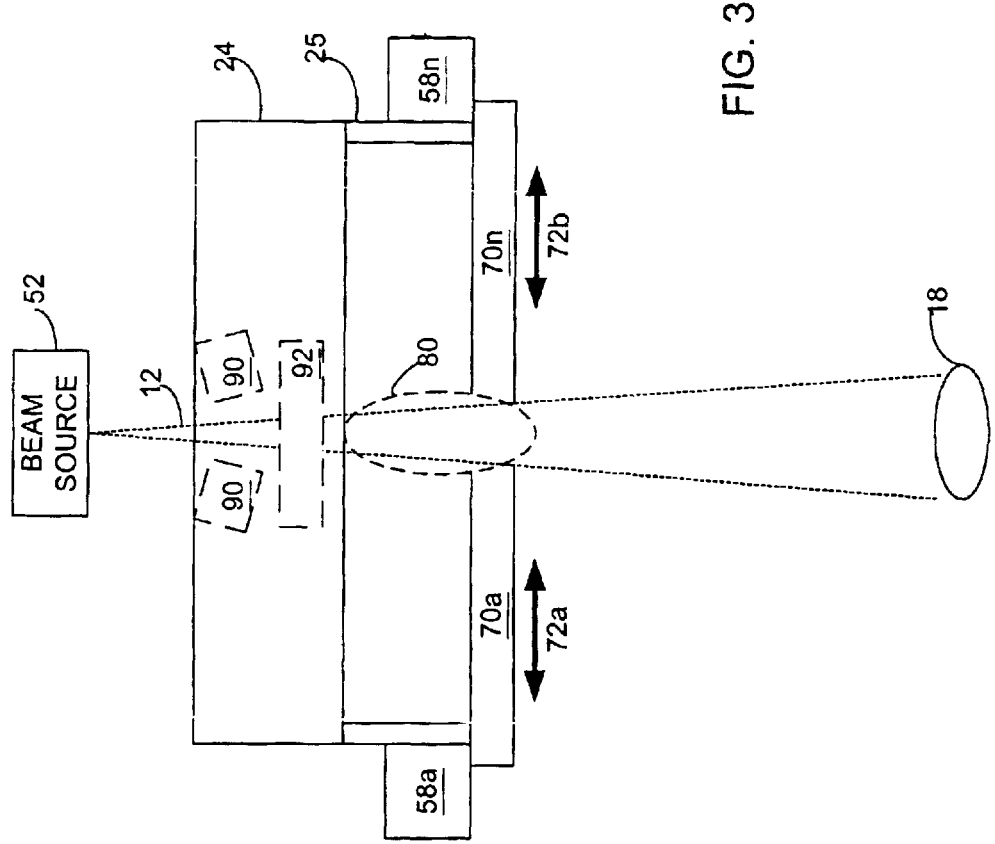
FIG. 3 is a diagram illustrating a treatment head for use in a radiation therapy device according to one embodiment of the present invention.

Referring now to FIG. 3, a perspective view of portions of radiation therapy device 10 is shown. In particular, FIG. 3 depicts portions of treatment head 24 as well as elements along a beam path 12. According to one embodiment of the present invention, treatment head 24 includes an accessory tray 25 or other mounting device positioned between treatment head 24 and treatment area 18. Components of a photon collimator (item 64 of FIG. 2) are shown as collimator blocks 90, 92 in FIG. 3. Collimator blocks 90, 92 are positioned within treatment head 24 and may include a number of individual elements or "leaves" which may be independently controlled to create a desired field shape at the isocenter. Any of a number of known collimators and shaping devices may be used as photon collimator (item 64 of FIG. 2) in conjunction with embodiments of the present invention.

According to one embodiment of the present invention, a separate electron collimator 62 is provided. According to one embodiment of the present invention, components of electron collimator 62 are removably mounted on accessory tray 25, allowing electron collimator 62 to be quickly installed and removed by radiation therapists or other technicians in order to add or remove electron field shaping capabilities to a radiation therapy device. According to one embodiment, individual leaf beds consisting of a number of individual collimator leaves 70a–n are mounted on accessory tray 25 such that they can be moved in a direction 72 across beam path 12. In one embodiment, the individual leaves 70a–n are formed of radiation attenuating materials. For example, brass or tungsten are currently preferred materials, although other materials with similar radiation attenuating characteristics may be used. In one embodiment, individual leaves 70a–n have a width of approximately 1–2 cm. Those skilled in the art will recognize that other shapes and sizes of individual leaves 70a–n may be selected to produce different field shapes at treatment zone 18.

Collimator drives 58a–n and other control circuitry are also removably mounted on accessory tray 25. In one embodiment, collimator drives 58a–n and other control circuitry are mounted on an exterior surface of accessory tray, away from beam path 12, providing greater durability and length of service for the electrical components used to operate electron collimator 62.

According to one embodiment of the present invention, a container 80 (such as a balloon or the like) filled with helium is positioned along a portion of beam path 12 to reduce the amount of free air along beam path 12. In one embodiment, container 80 is removably mounted to accessory tray 25. By replacing some of the air in the air column with helium (or another gas having a low density), the penumbra of the electron beam is reduced, allowing greater control over the shape and effect of the beam at the isocenter. In particular, use of helium along beam path 12 maintains the electron beam spread at a clinically acceptable level by decreasing the number of scattering interactions the electrons experience before they reach treatment zone 18. In operation, a shaped electron field may be delivered to treatment zone 18 by retracting leaves of photon collimator blocks 90, 92, passing the electron beam through helium-filled container 80, and selectively shaping the beam by manipulating electron collimator 62. Multiple fields can thus be delivered to treatment zone 18 during the course of a treatment without manual intervention. Further, embodiments of the present invention support mixed beam treatments by selectively switching between electron and photon beams. According to embodiments of the present invention, manual intervention and equipment set-up is reduced or eliminated.

Applicants have found that mounting components of electron collimator 62 on accessory tray 25 provides several desirable benefits. For example, during most types of treatments, electron collimator 62 provides sufficient patient clearance in all gantry and table positions. Further, electronic components, such as collimator drives 58a–n, will enjoy greater longevity because they are positioned away from beam path 12. Additionally, greater accuracy is provided during treatment because the overall swing weight of treatment head 24 and accessory tray 25 are minimized. The inventive configuration also enjoys the advantage of allowing ready removal and replacement of components. Accessory tray 25, in some embodiments, includes one or more accessory slots (not shown) into which components of electron collimator 62 may fit. In some embodiments, components of electron collimator 62 are installed by simply inserting the components into one or more accessory slots of accessory tray 25. As a result, for treatments that require greater clearance (e.g., such as photon treatments of breast cancer, etc.), components of electron collimator 62 may be readily removed, and then re-installed as needed.

Placement of components of electron collimator 62 on accessory tray 25 also serves to reduce the electron penumbra at the isocenter, providing greater accuracy in the delivery of electron treatments. Those skilled in the art will recognize that the electron penumbra can be reduced further by positioning components of electron collimator 62 closer to the isocenter; however, this increases problems with collision. In some embodiments, additional collision detection and avoidance components may be utilized in radiation therapy device 10 to reduce collisions and to allow closer positioning of components of electron collimator 62.

Figure 4:
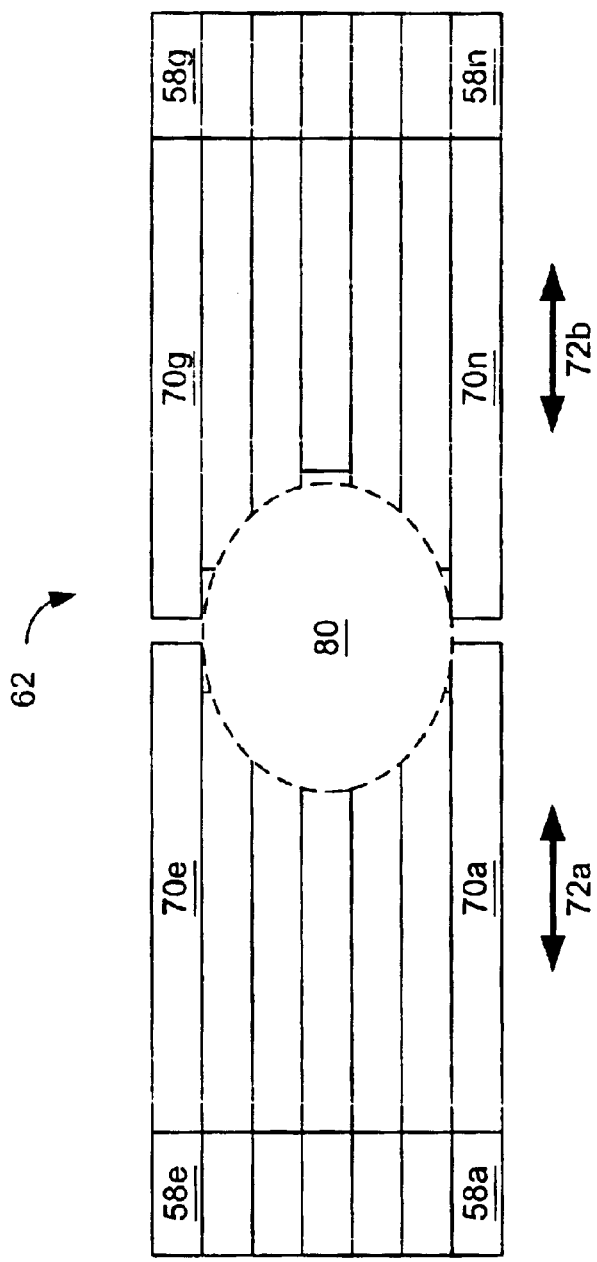
FIG. 4 is a diagram illustrating a collimator for use in a radiation therapy device according to one embodiment of the present invention.

Referring now to FIG. 4, details regarding the construction of electron collimator 62 are shown. FIG. 4 is a beams eye view of electron collimator 62, showing the placement of container 80 in relation to components of electron collimator 62. In one embodiment, electron collimator 62 includes a plurality of individual collimator drives 58a–n each coupled to drive individual leaves 70a–n of the collimator. As depicted, individual leaves 70a–n may be positioned using collimator drives 58a–n to generate a desired collimator shape, thereby producing a desired electron field shape at the treatment area on a patient.

Those skilled in the art will appreciate that various adaptations and modifications of the just described preferred embodiments can be configured without departing from the scope and spirit of the invention. Although a preferred embodiment utilizing removable electron collimator components has been described, in one embodiment, the electron collimator components may be mounted in a manner that does not facilitate ready removal. Therefore, it is to be understood that, within the scope of the appended claims, the invention may be practiced other than as specifically described herein.

What is claimed is:

1. A radiation therapy device, comprising:
    a radiation source positioned to direct a beam along a beam path toward a treatment area;
    a treatment head containing a first collimator controllable to selectively collimate said beam, the treatment head including an accessory tray mounted between said first collimator and said treatment area; and
    a second collimator removably mounted on said accessory tray and controllable to selectively collimate said beam, the second collimator including drive electronics removably mounted on an exterior of said accessory tray and a plurality of leaves removably mounted on said accessory tray and positionable by said drive electronics to move across said beam path.

2. The radiation therapy device of claim 1, wherein said first and said second collimators are controllable to selectively collimate said beam.

3. The radiation therapy device of claim 1, further comprising a first collimator drive operable to selectively position individual leafs of said first collimator.

4. The radiation therapy device of claim 1, further comprising:
    a helium-filled container positioned along said beam path between said beam source and said second collimator.

5. The radiation therapy device of claim 1, wherein said drive electronics of said second collimator positioned a distance from said beam path.

6. The radiation therapy device of claim 1, wherein said radiation source includes a photon radiation source and an electron radiation source.

7. The radiation therapy device of claim 6, wherein said first collimator is controllable to selectively collimate a photon beam generated by said photon radiation source.

8. The radiation therapy device of claim 6, wherein said second collimator is controllable to selectively collimate an electron beam generated by said electron radiation source.

9. The radiation therapy device of claim 1, further comprising a control unit coupled to said radiation source and to said first collimator and to said drive electronics of said second collimator to selectively deliver a prescribed dose of radiation to said treatment area.

10. The radiation therapy device of claim 9, wherein said control unit is operable to control said radiation source to generate a photon beam and to cause said drive electronics of said second collimator to position leaves of said second collimator away from said beam path to deliver a prescribed dose of photon radiation to said treatment area.

11. The radiation therapy device of claim 9, wherein said control unit is operable to control said radiation source to generate an electron beam and to cause said first collimator drive to position leaves of said first collimator away from said beam path to deliver a prescribed dose of electron radiation to said treatment area.

12. A radiation therapy system, comprising:
    a control unit;
    a treatment head having an enclosed area and an accessory tray;
    a photon radiation source, selectively operated by said control unit to generate a photon beam along a beam path from said treatment head toward a treatment zone;
    an election radiation source, selectively operated by said control unit to generate an electron beam along said beam path from said treatment head toward said treatment zone;
    a photon collimator, located between said photon radiation source and said treatment zone; and
    an electron collimator, removably mounted on said accessory tray, said electron collimator selectively positioned by said control unit to collimate said electron beam, the electron collimator including drive electronics removably mounted on an exterior of said accessory tray and a plurality of leaves removably mounted on said accessory tray and positionable by said drive electronics to move across said beam path.

13. An electron collimator for use in collimating an electron beam in a radiation therapy device, the collimator comprising:

drive electronics, removably mounted on an exterior of an accessory tray of said radiation therapy device; and a plurality of leaves positionable by said drive electronics to move across a path of said electron beam, said plurality of leaves removably mounted on said accessory tray of said radiation therapy device.

14. A radiation therapy device, comprising:

a radiation source positioned to selectively direct an electron beam and a photon beam along a beam path toward a treatment area;

a treatment head containing a first collimator controllable to selectively collimate said photon beam, and including an accessory tray positioned between the radiation source and the treatment area; and a second collimator removably mounted on said accessory tray and controllable to selectively collimate said electron beam, the second collimator including drive electronics removably mounted on an exterior of said accessory tray and a plurality of leaves removably mounted on said accessory tray and positionable by said drive electronics to move across said beam path.

15. A radiation therapy device, comprising:

a control unit;

a radiation source, controlled by said control unit to generate one of a photon beam and an electron beam along a beam path toward a treatment area;

a first collimator, positioned between said radiation source and said treatment area, said first collimator selectively positioned by said control unit to collimate said photon beam;

an accessory tray positioned between said first collimator and said treatment area; and a second collimator, removably mounted on said accessory tray, said second collimator selectively positioned by said control unit to collimate said electron beam, the second collimator including drive electronics removably mounted on an exterior of said accessory tray and a plurality of leaves removably mounted on said accessory tray and positionable by said drive electronics to move across said beam path.

16. The radiation therapy device of claim 15, further comprising:

a container positioned along said beam path between said first and second collimators.

17. The radiation therapy device of claim 16, wherein said container is filled with helium.

18. A radiation therapy method, comprising:

installing an external collimator on an accessory tray of a radiation therapy device such that drive electronics of said external collimator are mounted on an exterior of said accessory tray;

operating a radiation source to direct a beam from a treatment head along a beam path toward a treatment area;

selectively controlling an internal collimator to collimate said beam;

selectively controlling said external collimator to collimate said beam, said external collimator removably positioned between said internal collimator and said treatment area.

19. A radiation therapy method, comprising:

installing an external collimator on an accessory tray of a radiation therapy device such that drive electronics of said external collimator are mounted on an exterior of said accessory tray:

selecting between an electron treatment beam and a photon treatment beam;

directing said selected beam from a radiation source along a beam path toward a treatment area;

selectively controlling a photon collimator to collimate said selected beam if said selected beam is said photon beam; and selectively controlling said external collimator to collimate said selected beam if said selected beam is said electron beam, wherein said external collimator is positioned between said photon collimator and said treatment area.

* * * * *